(12) United States Patent
Yang

(10) Patent No.: US 9,474,600 B2
(45) Date of Patent: Oct. 25, 2016

(54) PROSTHETIC HEART VALVE

(75) Inventor: Jun Yang, Shanghai (CN)

(73) Assignee: Shanghai Cingular Biotech Corporation (CN)

( * ) Notice: Subject to any disclaimer, the term of this patent is extended or adjusted under 35 U.S.C. 154(b) by 0 days.

(21) Appl. No.: 14/403,374

(22) PCT Filed: May 24, 2012

(86) PCT No.: PCT/CN2012/075988
§ 371 (c)(1),
(2), (4) Date: Nov. 24, 2014

(87) PCT Pub. No.: WO2013/173997
PCT Pub. Date: Nov. 28, 2013

(65) Prior Publication Data
US 2015/0289972 A1    Oct. 15, 2015

(51) Int. Cl.
*A61F 2/24* (2006.01)
(52) U.S. Cl.
CPC ........... *A61F 2/2409* (2013.01); *A61F 2/2412* (2013.01); *A61F 2/2418* (2013.01); *A61F 2210/0076* (2013.01); *A61F 2220/0075* (2013.01)
(58) Field of Classification Search
CPC .. A61F 2/2418; A61F 2/2412; A61F 2/2409; A61F 2210/0076
See application file for complete search history.

(56) References Cited

U.S. PATENT DOCUMENTS

| 5,928,281 A | 7/1999 | Huynh et al. |
| 2004/0176839 A1 | 9/2004 | Huynh et al. |
| 2007/0067029 A1 | 3/2007 | Gabbay |
| 2008/0294247 A1 | 11/2008 | Yang et al. |
| 2008/0294248 A1 | 11/2008 | Yang et al. |
| 2009/0210052 A1 | 8/2009 | Forster et al. |
| 2010/0179641 A1 | 7/2010 | Ryan et al. |

FOREIGN PATENT DOCUMENTS

| CA | 1229701 | 1/2016 |
| CN | 201040046 | 3/2008 |
| CN | 101711139 | 5/2010 |
| CN | 101715330 A | 5/2010 |
| CN | 102652694 | 9/2012 |
| CN | 202589707 | 12/2012 |

*Primary Examiner* — Brian Dukert
(74) *Attorney, Agent, or Firm* — Blank Rome LLP

(57) ABSTRACT

The present invention provides a prosthetic heart valve comprising a stent, an alloy wire and biological tissue leaflets, the biological tissue leaflets being sewn to the alloy wire which is wrapped with a first polyester cloth, and the alloy wire being sewn to the stent which is wrapped with a second polyester cloth, wherein the stent is ring-shaped, comprising: a first stent layer and a second stent layer which are closely hooping with each other; the first stem layer being on the outside of the second stent layer, the first stent layer being made of a first material, the second stent layer being made of a second material, the first material and the second material being elastic, and the hardness of the second material being higher than that of the first material. Through the design of making the stent always tend to remain annular both in a stationary state and in a stressed state, the prosthetic heart valve of the present invention ensures the perfect match between the stent and the alloy wire, thereby increasing the stability of the entire valve and extending the service life of the valve.

7 Claims, 4 Drawing Sheets

PROSTHETIC HEART VALVE

RELATED APPLICATION

This is a national phase of PCT/CN2012/075988, filed May 24, 2012. The content of this application is hereby incorporated by reference.

FIELD OF THE INVENTION

The present invention relates to a prosthetic heart valve, particularly relates to a bioprosthetic valve, and more particularly relates to astent bioprosthetic valve.

DESCRIPTION OF THE PRIOR ART

The human heart has four valves controlling the direction of blood flow. The aortic valve and the mitral valve are on the left side of the heart, controlling the flow of oxygen-rich arterial blood from the lungs to the whole body. The pulmonary valve and the tricuspid valve are on the right side of the heart, controlling the flow of oxygen-depleted venous blood back into the lungs from the whole body. The aortic valve lies between the left ventricle and the aorta, and the pulmonary valve lies between the right ventricle and the pulmonary artery, which prevents the back flow of the blood pumped from the ventricle. The mitral valve and the tricuspid valve lie between the atria and the ventricles, preventing the back flow of the blood into the atria.

The left ventricle is the heart's main chamber to supply blood to the whole body. Therefore, the consequence of dysfunction of the aortic valve and the mitral valve on the left side of the heart is usually more serious than that of the other two valves. The aortic valve is prone to stenosis due to the accumulation of calcified materials on the leaflets. When the lesion occurs, a replacement therapy is usually required. Although the aortic valve with incomplete closure in some cases can be repaired, the replacement is also a good choice. In developed countries, common mitral valve cases are caused by the elongation of the chordae tendincae and myocardial ischemia; while in developing countries and gathering areas where the majority of immigrants are from developing countries, common mitral valve cases are caused by rheumatic heart disease, and in such cases, the valve can not be repaired but to be replaced.

The atrium and ventricle on the right side of the heart have smaller blood supply load than those on the left side, so dysfunction of the pulmonary valve and the tricuspid valve on the right side is relatively rare. The pulmonary valve has similar structure and function with the aortic valve, and the dysfunction of which is usually associated with congenital heart defects. A replacement surgery of the pulmonary valve will be carried out on the adults with congenital heart disease depends on situations. The tricuspid valve is anatomically and functionally similar to the mitral valve, having a valve annulus, chords and papillary muscles, but having three leaflets (an anterior leaflet, a posterior leaflet and a septal leaflet). The shape of valve annulus of the tricuspid valve is more snail-shaped and is asymmetry in shape, which is also different from that of the mitral valve.

The heart valves are passive structures, and the opening and the closure of the valve are simply in response to the differential pressures on the either side of the specific valve. Therefore, the problems of the valves can be divided into two kinds: (1) Pathological stenosis, in which the valve fails to open normally; (2) Insufficiency (also called regurgitation), in which the valve fails to close completely. The incomplete opening of the valve leads to valvular stenosis and thus obstructing the blood flow, while the incomplete closure of the valve results in the back flow of the blood. Valve stenosis and insufficiency may co-exist in the same valve or in different valves. Both of the conditions increase the burden on the heart, and the situation is not optimistic. The more serious the situation is, the greater the impact is on the patient. The heart tolerance to these two conditions determines whether the replacement or (in some cases) repair of the valve by surgery is necessary. If untreated, both of the conditions will lead to gradual heart failure and result in death of the patient finally.

Congenital or acquired heart disease will cause anatomical or functional abnormalities of heart valves which threatening the life of a patient. Therefore these diseases need to be treated. There are usually two kinds of treatments: one is to repair the valve on the basis of keeping the original one; the other is to replace the original diseased valve with an artificial one. Since all the prosthetic valves have their own defects (e.g., a lifelong need of anticoagulant, risk of thrombosis, limited durability), if the lesion of the valve is not serious, the preferred choice is repair rather than replacement of the valve. However, in practice, many dysfunctional valves can not be treated through repair. For instance, a patient suffering from rheumatic heart disease is not suitable for mitral valve repair. Therefore, in most cases, the treatment is carried out through replacing the valve with an artificial one.

The currently known prosthetic heart valves have two basic types. One is mechanical valve, which is made of non-biologically originated materials; the other is bioprosthetic valve, the valve leaflets of which is made of biological tissue material, mimicking the morphologic function and the working mechanism of human heart valve itself.

These two prosthetic heart valves have their own advantages and disadvantages. As for the clinical effect, the mechanical valve has the longest service life. However, patients having received mechanical valve implant surgery have to take anticoagulant for life and need regular checks of coagulation parameters in order to prevent the occurrence of thrombosis. While the use of too much anticoagulant may increase the risk of bleeding and this is very disadvantageous to the patients. In addition, the noise of a working mechanical valve is relatively big, and the mechanical valve may suddenly fail to work without any warning, and incarceration or prolapse may occur to the leaflets, causing serious consequences, even death of the patient.

The bioprosthetic valve works without noise and generally has little affect on the normal blood flow, which makes it different from the mechanical one. And the patient who has received a bioprosthetic valve implantation does not need to take anticoagulant. However, with the passage of time, some natural processes in the human body may gradually make the bioprosthetic leaflets become stiff or calcified, particularly the high-stress areas of the leaflets, such as the junctions between the leaflets and the surrounding attachment points of the leaflets or the 'cusps' at the outer edge of each leaflet. In addition, the leaflets are subject to continuous stress from the opening and closure. So the bioprosthetic valve will eventually be worn out and still need to be replaced by a new one. Because the bioprosthetic valves are generally handmade and are made by specially trained and skilled personnel, it is very time-consuming and is more difficult than producing mechanical valves.

The bioprosthetic valves include intact allograft valves from volunteers or cadavers, allograft valves made of the materials acquired from volunteers, autograft valves made of the materials acquired from the patients themselves who receive the surgery, as well as heterograft valves from pigs, horses or cattle and the like.

There are two types of design structures in the current used heterograft bioprosthetic valves: one is to sew the leaflets of porcine aortic valve onto an alloy wire/stent, the other is to make the leaflets with pericardia of cattle, horses, pigs or other animals and sew the leaflets onto a alloy wire/stent opposite each other, such as bovine pericardial valve. The bovine pericardial valve of Carpentier-Edwards Perimount™ has been sale which is a successful case of the latter one. The alloy wire of the valve matches the stent in an upper and lower manner and clamps the leaflets in the middle. Regardless of the type, the heterograft valve's alloy wire/stent is constructed to provide a stable three-dimensional support structure for the valve leaflets which imparts a certain degree of flexibility to reduce stress on the leaflet during valve opening and closure. The alloy wire/stent is covered with a biocompatible cloth (usually a polyester material such as polyester or PTFE), on which the leaflets are sewn, and the valve sewing ring is wrapped in a cloth. During the surgery of valve replacement, the valve is sewn to the corresponding position of the patient's heart from position of the sewing ring.

Even after decades of continuous improvement, the existing bioprosthetic valves still have some drawbacks. One of the drawbacks is the low matching degree between the alloy wire and the stent, which is often due to the deformation of the ring structure. Prior art stent is fabricated from a length of resilient material which is bent into a circular ring structure and whose ends are welded together. This producing process makes the stent susceptible to spring-back effect of the material and undergo deformation. The stress applied to the stent upon sewing it together with the alloy wire, and that experienced during normal functioning of the valve, makes the stent further susceptible to deformation, resulting in dislocation between the alloy wire and the stent. FIG. 1 shows the mismatch existing between the circular alloy wire 2 and the annular stent 1. There is a gap 21, and the stent is oval rather than round. This mismatch often leads to a shift of the alloy wire from the stent, which reduces the stability of the entire valve, and thus resulting in uneven stress on the valve, especially on the valve leaflets, which leads to wrinkles, expedites wearing of the valve and reduces the service life.

Accordingly, there is still room for improvement in the stability and performance of the bioprosthetic valve and for improvement in fabricating techniques of the valve. The present invention seeks to address the aforementioned shortcoming while maintaining the necessary structural and functional features and ensuring functional longevity of the valve.

SUMMARY OF THE INVENTION

In order to solve the problem described above, the present invention provides a novel prosthetic heart valve, which through making the stent tend to remain annular both in a stationary state and in a stressed state ensures perfect match between the stent and the alloy wire, thereby increasing the overall stability of the valve and extending its service life.

The prosthetic heart valve of the present invention comprises a stent, an alloy wire and biological tissue leaflets. The biological tissue leaflets are sewn to the alloy wire which is wrapped with a first polyester cloth, and the alloy wire is sewn to the stent which is wrapped with a second polyester cloth, wherein the stent is ring-shaped, which comprising: a first stent layer and a second stent layer which are closely hooping with each other; the first stent layer being on the outside of the second stent layer, the first stent layer being made of a first material, the second stent layer being made of a second material, the first material and the second material being elastic materials, and the hardness of the second material being higher than that of the first material.

Preferably, the first stent layer and the second stent layer is configured to: before the first stent layer is hooped on the second stent layer, the inner diameter of the first stent layer is smaller than the outer diameter of the second stent layer.

In the prosthetic heart valve of the present invention, the stent consists of at least two layers of ring. One layer is a ring of higher hardness (e.g., made of Elgiloy superalloy), one layer is a ring of better elasticity (e.g., made of polymer material, such as PET), and the inner diameter of the outer ring can be slightly smaller than the outer diameter of the inner ring before assembly. If the inner layer is a ring has higher hardness while the outer layer is a ring has better elasticity, the outer ring produces a confining effect on the inner ring; if the outer layer is a ring has higher hardness and the inner layer is a ring has better elasticity, the inner ring produces a pushing effect on the outer ring; and the former situation has a more significant effect on making the entire stent tent to be annular.

Preferably, the stent may further comprise a third stent layer and the third stent layer is closely hooped by the second stent layer with the second stent on the outside of the third stent layer. More preferably, the end edges of both first stent layer and third stent layer extend beyond the end edge of the second stent layer towards the outlet side of said prosthetic heart valve. In this way, the end edge of the outlet side of the three-layer ring forms a groove structure, which can restrict the movement of the alloy wire inward or outward the stent, making the alloy wire combine with the stent more tightly, and making the entire valve structure be more stable. The third stent layer may be made of polymer materials, such as PET.

Both the two-layer ring and the three-layer ring mentioned above can be manufactured by machining or casting into seamless ones, and they can also be manufactured by welding. In the case of welding, attention should be paid to that when hooping each ring, every two welding point should be separated from the each other.

The prosthetic heart valve provided by the invention can be used in open heart surgery to replace the valve with lesions—primarily the aortic valve and the mitral valve.

On the basis of retaining the basic structure and function of the original valve, the beneficial effects of the present invention is improving the stability of the valve in the following aspects: (1) The basic structure of the stent is a nest of two layers of ring and the inner diameter of the outer ring is slightly smaller than the outer diameter of the inner ring, wherein the outer ring is a closed ring. The force produced by hooping the inner ring makes the inner ring tend to be circular in both stationary state and stressed state. Furthermore, the flexibility of the outer ring is better; the inner ring is of higher hardness and slight elasticity, which makes the inner ring difficult to deform into a non-circular shape under stress, so that the stent tends to be annular all the time and maintains a good match with the alloy wire. This takes advantage of the isoperimetric theorem of geometry: among the geometries of equal closed area on the Euclidean plane, circle has the smallest circumference. (2) If an additional third ring is added on the inside of the nested two-layer structure, making the outlet side of the three-layer ring form a groove, the inward or outward movement of the alloy wire can be restricted to make the combination with the stent more tight and the entire valve structure more stable.

A further description will be made as to the conception, detailed structure, and expected technical effects of the present invention with reference to the accompanying drawings to make the objects, features, and effects of the present invention fully understood by the person skilled in the art.

DETAILED DESCRIPTION OF THE PREFERRED EMBODIMENTS

Figure 1:
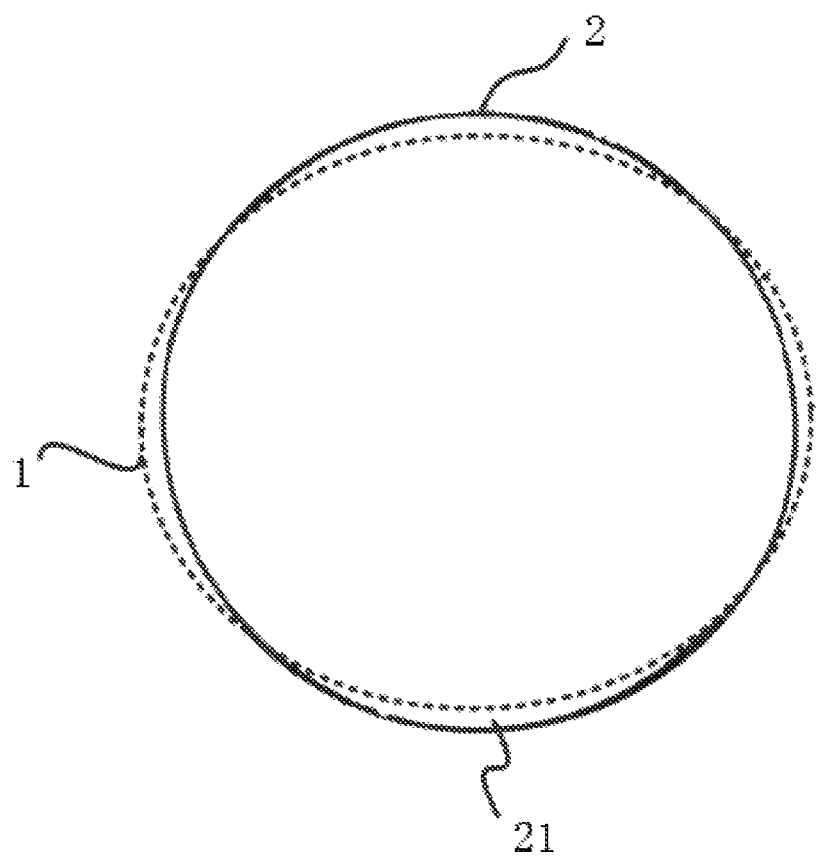
FIG. 1 is a schematic of a top view from the outlet side of the alloy wire and the stent main body of a prior art prosthetic heart valve.
Figure 2:
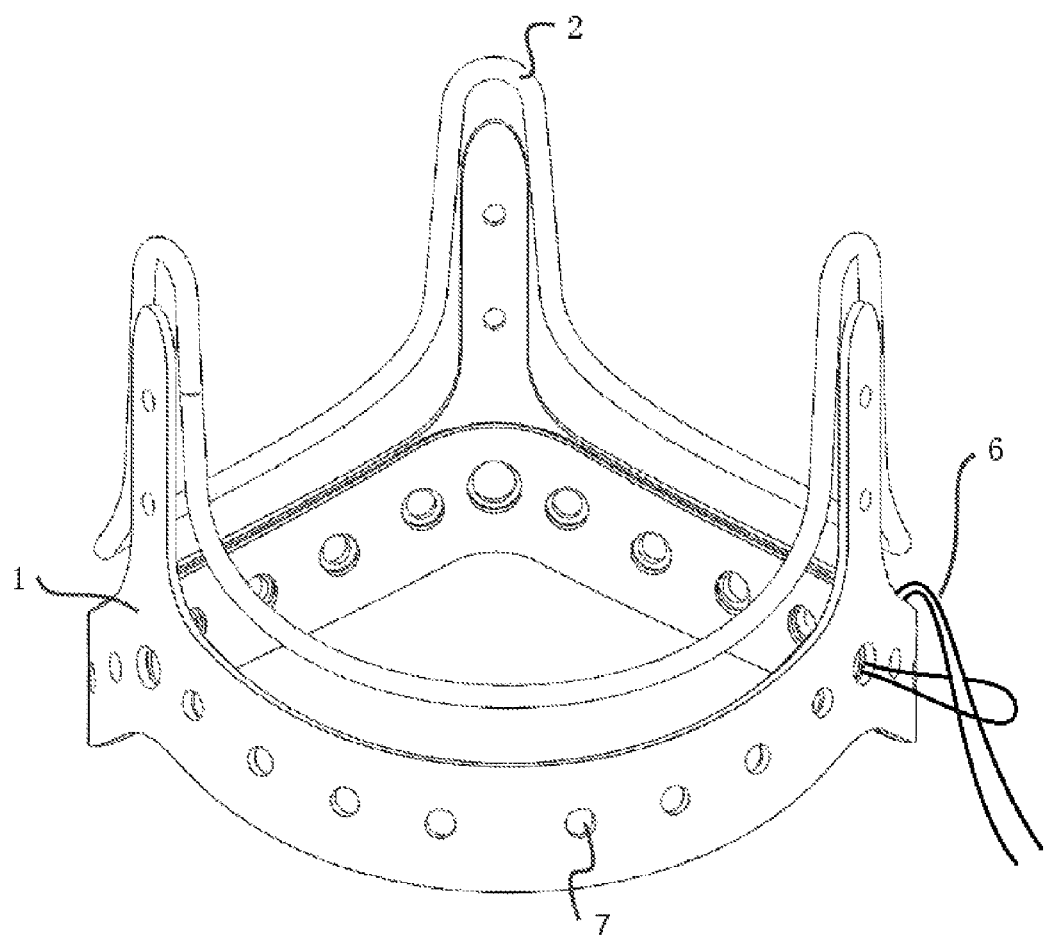
FIG. 2 is a three-dimensional structural view showing the first embodiment of the prosthetic heart valve provided by the present invention.
Figure 3:
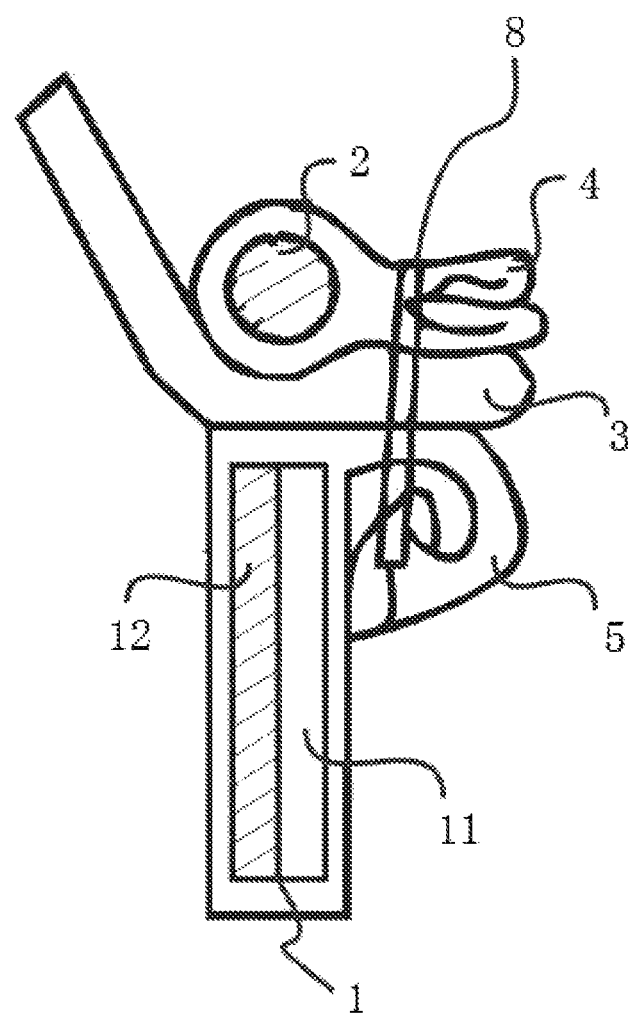
FIG. 3 is a sectional structural view showing the first embodiment of the prosthetic heart valve provided by the present invention.

FIG. 2 and FIG. 3 show a first embodiment of the prosthetic heart valve provided by the present invention. As shown in FIG. 2 and FIG. 3, the prosthetic heart valve in the embodiment includes a stent 1, an alloy wire 2 and biological tissue leaflets 3, the biological tissue leaflets 3 being sewn to the alloy wire 2 which is wrapped with a first polyester cloth 4, and the alloy wire 2 being sewn to the stent 1 which is wrapped with a second polyester cloth 5, wherein the stent 1 is ring-shaped, comprising a first stent layer 11 and a second stent layer 12 closely hooping with each other: the first stent layer 11 being made of PET, the second stent layer being made of Elgiloy superalloy, the alloy wire 2 being made of Elgiloy superalloy. Both the first stent layer and the second stent layer are arranged with a plurality of round holes 7 aligned with each other, and through the round holes 7, the first stent layer and the second stent layer are fixed by suture 6.

Furthermore, prior to assembly, the inner diameter of the first stent layer 11 is slightly smaller than the outer diameter of the second stent layer 12. Upon assembly, the second stent layer 12 is hooped with the first stent layer 11 tightly and in alignment, making the stent 1 tend to be circular in both stationary state and stressed state. Subsequently, the two layers of ring are wrapped with a second polyester cloth 5 and are fixed with suture 6 through the round holes 7 which are in pairwise alignment. Then the biological tissue leaflets 3 are sewn to the alloy wire 2 wrapped with the first polyester cloth 4, and then fixed to the stent 1 wrapped with the second polyester cloth 5.

Figure 4:
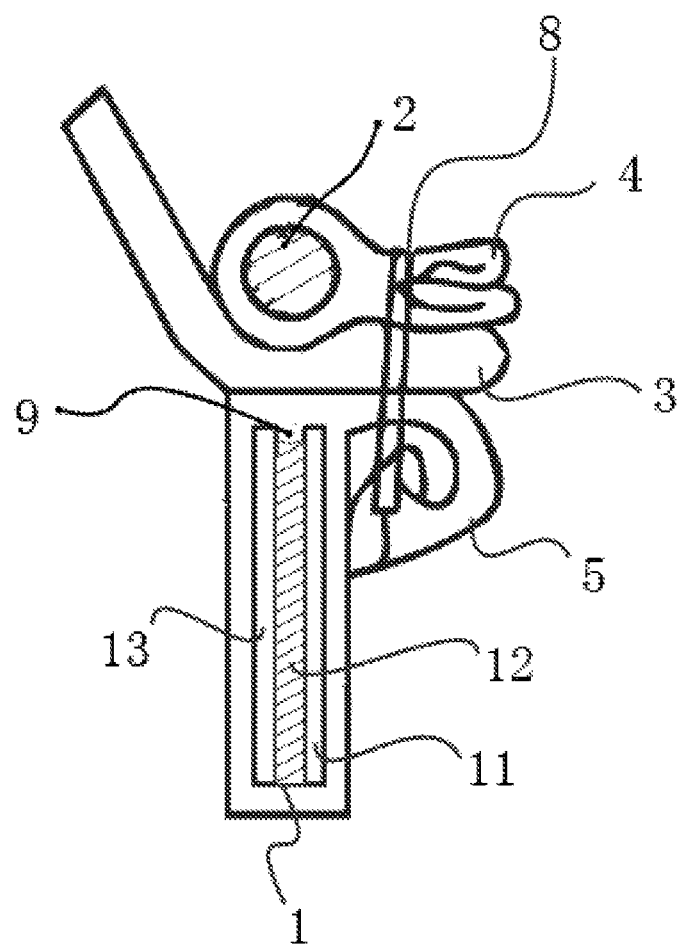
FIG. 4 is a sectional structural view showing the second embodiment of the prosthetic heart valve provided by the present invention.

FIG. 4 shows a second embodiment of the prosthetic heart valve provided by the present invention. As shown in FIG. 4, the prosthetic heart valve in the embodiment includes a stent 1, a alloy wire 2 and biological tissue leaflets 3, the biological tissue leaflets 3 being sewn to the alloy wire 2 which is wrapped with a first polyester cloth 4, and the alloy wire 2 being sewn to the stent 1 which is wrapped with a second polyester cloth 5, wherein the stent 1 is ring-shaped, having three layers of ring, i.e., comprising a first stent layer 11, a second stent layer 12 and a third stent layer 13. The first stent layer 11 is made of PET; the second stent layer is made of Elgiloy superalloy; the third stent layer is made of PET.

The material of the second stent layer 12 in the middle is of higher hardness, while the material of the outermost first stent layer 11 is of relative lower hardness and better flexibility, and prior to assembly, the outer diameter of the second stent layer 12 is slightly smaller than the inner diameter of the first stent layer 11. The first stent 11, the second stent 12 and the third stent 13 are further arranged with a plurality of round holes 7 aligned with each other; the first stent 11, the second stent 12 and the third stent 13 are fixed by suture through the round holes. The innermost third stent layer 13 is as wide as the first stent layer 11, and is slightly wider than the second stent layer 12. Upon assembly, the third stent layer 13 is first hooped with the second stent layer 12; the second stent layer 12 is then hooped with the first stent layer 11. During assembly, the end edges on the inlet side of the first stent layer 11, the second stent layer 12 and the third stent layer 13 are kept aligned. So a structure of groove 9 is formed on the outlet side. Subsequently, the three layers of ring are fixed with suture 6 through the round holes 7, which are in pairwise alignment, and then the three layers of ring are wrapped with the second polyester cloth 5. After sewing the biological tissue leaflets 3 to the alloy wire 2 wrapped with the first polyester cloth 4, fixing them to the stent 1 which is wrapped with the second polyester cloth 5.

The invention has been exemplified above with reference to specific embodiments. However, it should be understood that a multitude of modifications and varieties can be made by a common person skilled in the art based on the conception of the present invention. Therefore, any technical schemes, acquired by the person skilled in the art based on the conception of the present invention through logical analyses, deductions or limited experiments, fall within the scope of the invention as specified in the claims.

The invention claimed is:

1. A prosthetic heart valve comprising a stent, an alloy wire and biological tissue leaflets, wherein:
    said biological tissue leaflets is sewn to said alloy wire which is wrapped with a first polyester cloth, and said alloy wire is sewn to the stent which is wrapped with a second polyester cloth; and
    said stent is ring-shaped and comprises a first stent layer made of a first material and a second stent layer made of a second material;
    wherein, said second stent layer is closely hooped by said first stent layer with said first stent layer on the outside of said second stent layer, and said first material and said second material are elastic materials, and the hardness of said second material is higher than that of said first material;
    wherein said first stent layer and said second stent layer are configured that the inner diameter of said first stent layer is smaller than the outer diameter of said second stent layer.

2. The prosthetic heart valve according to claim 1, wherein said first material is PET.

3. The prosthetic heart valve according to claim 1, wherein said second material is Elgiloy superalloy.

4. The prosthetic heart valve according to claim 1, wherein said alloy wire is made of Elgiloy superalloy.

5. The prosthetic heart valve according to claim 1, wherein said stent further comprises a third stent layer and said third stent layer is closely hooped by said second stent layer with said second stent on the outside and said third stent layer on the inside.

6. The prosthetic heart valve according to claim 5, wherein end edges of both said first stent layer and said third stent layer extend beyond an end edge of said second stent layer towards the outlet side of said prosthetic heart valve.

7. The prosthetic heart valve according to claim 5, wherein said third stent layer is made of PET.

* * * * *